United States Patent
Ochiai et al.

(10) Patent No.: US 9,457,134 B2
(45) Date of Patent: *Oct. 4, 2016

(54) SURFACE TREATING AGENT, FILTERING MATERIAL FOR FILTER, AND BLOOD TREATMENT FILTER

(71) Applicant: TERUMO KABUSHIKI KAISHA, Shibuya-ku, Tokyo (JP)

(72) Inventors: Shoji Ochiai, Kanagawa (JP); Norifumi Tokunaga, Kanagawa (JP); Noboru Taguchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,090

(22) Filed: Oct. 7, 2015

(65) Prior Publication Data

US 2016/0024240 A1 Jan. 28, 2016

Related U.S. Application Data

(63) Continuation of application No. 13/259,359, filed as application No. PCT/JP2010/054460 on Mar. 16, 2010, now Pat. No. 9,186,441.

(30) Foreign Application Priority Data

Mar. 30, 2009 (JP) .................................. 2009-083034

(51) Int. Cl.
| | |
|---|---|
| *B01D 29/00* | (2006.01) |
| *C08F 220/26* | (2006.01) |
| *C08F 220/28* | (2006.01) |
| *C09D 133/08* | (2006.01) |

(Continued)

(52) U.S. Cl.
CPC ........... *A61L 33/064* (2013.01); *A61M 1/3633* (2013.01); *B01D 29/00* (2013.01);
(Continued)

(58) Field of Classification Search
CPC ............. A61L 33/0088; A61L 33/064; C08F 220/26; C08F 220/56; C08F 220/28; C08F 220/285; B01D 29/00; B01D 71/64; B01D 39/1623; A61M 1/3633; A61M 2202/0439; C09D 133/24; C09D 133/14; C09D 133/08; C09D 133/10

See application file for complete search history.

(56) References Cited

U.S. PATENT DOCUMENTS

| | | |
|---|---|---|
| 4,936,998 A | 6/1990 | Nishimura et al. |
| 5,476,587 A | 12/1995 | Kuroki et al. |

(Continued)

FOREIGN PATENT DOCUMENTS

| | | |
|---|---|---|
| CN | 1489485 A | 4/2004 |
| CN | 100457200 C | 2/2009 |

(Continued)

OTHER PUBLICATIONS

International Search Report (PCT/ISA/210) mailed on May 18, 2010, by the Japanese Patent Office as the International Searching Authority for International Application No. PCT/JP2010/054460.

(Continued)

*Primary Examiner* — John Kim
(74) *Attorney, Agent, or Firm* — Buchanan, Ingersoll & Rooney PC

(57) ABSTRACT

A surface treating agent comprising a copolymer including: a monomer (A) having a hydrophilic functional group of formula (1), a monomer (B) having a basic functional group of formula (3) or (5), and a monomer (C) having a reactive functional group of formula (7), wherein the copolymer has a molar ratio of the monomer (A)/the monomer (B)/and the monomer (C) between 87/10/3 and 98/1/1. In the formulas, the R groups and n are defined.

$$CH_2=CR^1 \quad\quad (1)$$
$$\quad | $$
$$COO-C_nH_{2n}-O-R^2$$

$$CH_2=CR^5 \quad\quad (3)$$
$$\quad | $$
$$COO-C_nH_{2n}-N-R^6$$
$$\quad\quad\quad\quad\quad\quad | $$
$$\quad\quad\quad\quad\quad\quad R^6$$

$$CH_2=CR^5 \quad\quad (5)$$
$$\quad | $$
$$CONH-C_nH_{2n}-N-R^6$$
$$\quad\quad\quad\quad\quad\quad\quad | $$
$$\quad\quad\quad\quad\quad\quad\quad R^6$$

$$CH_2=CR^7 \quad\quad (7)$$
$$\quad | $$
$$COO-C_nH_{2n}-Y$$

6 Claims, 1 Drawing Sheet

(51) Int. Cl.
  *C09D 133/10* (2006.01)
  *A61L 33/06* (2006.01)
  *A61M 1/36* (2006.01)
  *C08F 220/56* (2006.01)

(52) U.S. Cl.
  CPC .......... *C08F 220/26* (2013.01); *C08F 220/28* (2013.01); *C09D 133/08* (2013.01); *C09D 133/10* (2013.01); *C08F 220/56* (2013.01); *C08F 2220/285* (2013.01)

(56) References Cited

U.S. PATENT DOCUMENTS

| | | | |
|---|---|---|---|
| 6,590,054 | B2 | 7/2003 | Tanaka et al. |
| 2005/0014127 | A1 | 1/2005 | Onodera et al. |
| 2009/0173685 | A1 | 7/2009 | Imai et al. |

FOREIGN PATENT DOCUMENTS

| | | | |
|---|---|---|---|
| EP | 1356855 | A1 | 10/2003 |
| JP | 6-51060 | B2 | 7/1994 |
| JP | H07-124255 | A | 5/1995 |
| JP | 2002-105136 | A | 4/2002 |
| JP | 3379972 | B2 | 2/2003 |
| JP | 2003-70905 | A | 3/2003 |
| JP | 2003-164522 | A | 6/2003 |
| JP | 2003-190276 | A | 7/2003 |
| JP | 2004-339165 | A | 12/2004 |
| WO | WO 03/051941 | A1 | 6/2003 |
| WO | WO 2006/016163 | A1 | 2/2006 |
| WO | WO 2007/145328 | A1 | 12/2007 |

OTHER PUBLICATIONS

Office Action issued on Sep. 26, 2013, in corresponding Chinese Patent Application No. 201080005047.7 and English translation of the office action (21 pages).

Extended Search Report issued in corresponding European Patent Application No. 10758408 dated Feb. 12, 2014.

Office Action (Notice of Reasons for Rejection) issued by the Japanese Patent Office in corresponding Japanese Patent Application No. 2015-029086 on Dec. 22, 2015 (8 pages including English translation).

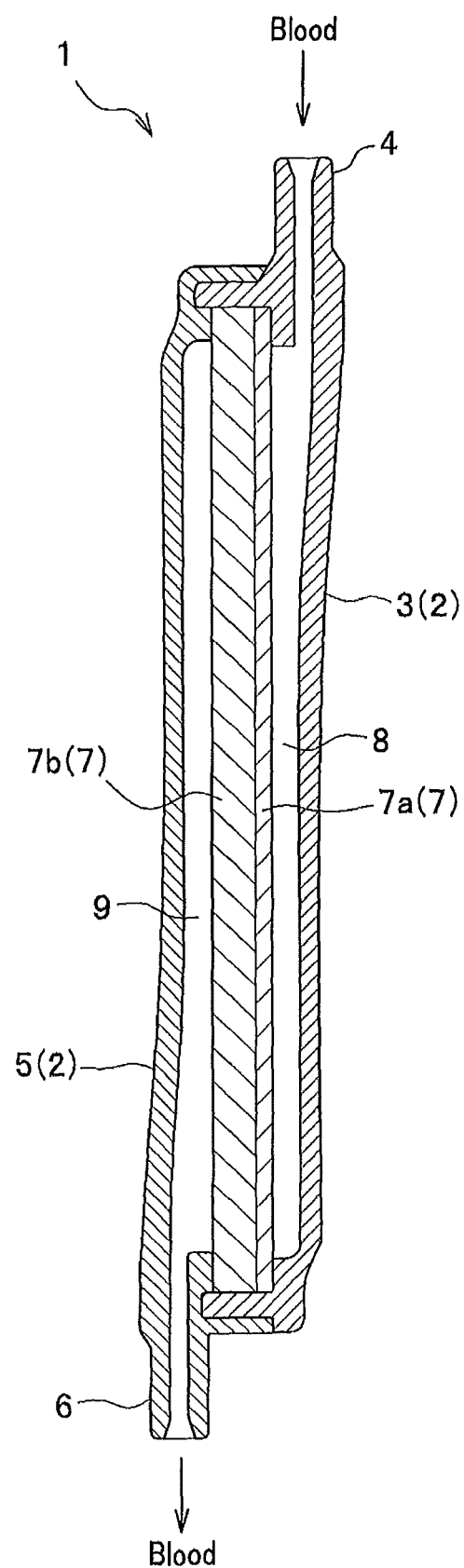

SURFACE TREATING AGENT, FILTERING MATERIAL FOR FILTER, AND BLOOD TREATMENT FILTER

This application is a continuation of U.S. application Ser. No. 13/259,359 filed on Sep. 23, 2011, issued as U.S. Pat. No. 9,186,441, which is a National Stage of International Application No. PCT/JP2010/054460 filed on Mar. 16, 2010, and claims priority to Japanese Application No. 2009-083034 filed on Mar. 30, 2009, the entire contents of all three of which is incorporated herein by reference.

FIELD OF THE INVENTION

The present invention relates to a medical device, particularly, a surface treating agent with which a blood contact surface of a base material that is used for a blood treatment filter is coated, a filtering material having the base material coated with the surface treating agent and a blood treatment filter.

DESCRIPTION OF THE RELATED ART

Recently, various polymer materials have been used for base materials which are used for medical device. Polymer materials that are foreign to organisms are in contact with blood while being used, therefore, the base material is required to inhibit property of adhesion and activation of platelets (antithrombotic performance). To meet the requirement, the base material coated with a certain surface treating agent on the surface is used in general. Further, in a case where the base material is used for a blood treatment filter as a medical device, the base material must have an excellent blood filtration property (specifically, leukocyte removal rate, platelet collection rate and the like).

Patent Literature 1 (described below) discloses a polymer having a nonionic hydrophilic group and a nitrogen-containing basic functional group as a surface treatment agent for blood treatment filter, specifically, a copolymer of hydroxyethyl methacrylate and diethylaminoethyl methacrylate. Patent Literature 1 discloses that by coating a filtering material (a base material) with the copolymer a leukocyte removal ratio and a platelet passage (collection) ratio become higher.

Patent Literature 2 (described below) discloses a copolymer including alkoxyalkyl methacrylate and a monomer having a basic functional group (aminoalkyl methacrylates, aminoalkyl methacrylamides or the derivatives thereof) as a surface treatment agent for blood treatment filter. Patent Literature 2 discloses that by covering a surface of a medical device (a base material) with the copolymer, both the leukocyte removal ratio and the platelet collection ratio become higher.

Patent Literature 3 (described below) discloses a cationic material having a quaternary nitrogen on the main chain or side chain as a surface treatment agent. Patent Literature 3 (described below) discloses that by bonding a surface of a base material with the cationic material, leukocyte removal ratio is improved.

PRIOR ART DOCUMENTS

Patent Literatures

Patent Literature 1: JP Hei 06-51060 B1 (1994) (corresponding to U.S. Pat. No. 4,936,998 A)

Patent Literature 2: JP 2002-105136 A (corresponding to U.S. Pat. No. 6,590,054 B2)

Patent Literature 3: JP 3379972 B2

SUMMARY OF INVENTION

Problem to be Solved by the Invention

However, the surface treating agent described in PATENT LITERATURE 1 or 2 bonds weakly with the base material (fixes insufficiently to the base material). Therefore, through sterilizing or washing of the medical device, or contacting of the medical device repeatedly with blood, the surface treating agent tends to detach (elute) easily from the base material which causes a problem that the antithrombotic performance is not maintained. Further, leukocytes are adsorbed using the surface treating agent described in PATENT LITERATURE 3. In spite of the improvement of leukocyte removal rate, platelets are simultaneously adsorbed (adhered) with leukocytes. Therefore, it causes a problem that the platelet collection rate decreases. At the same time the adhered platelets are activated which causes a problem that antithrombotic level is insufficient.

The present invention has been created in view of the above-mentioned problem. Herein, an object of the present invention is to provide a surface treating agent. When a blood contact surface of a base material that is used for a medical device is coated with the surface treating agent, the surface treating agent not only can fix the base material effectively and maintain an excellent antithrombotic performance, but also can show excellent leukocyte removal ability and excellent platelet collection rate when a base material of a blood treatment filter is coated with the surface treating agent. Another object of the present invention is to provide a filtering material for filter coated with the surface treating agent. Still another object of the present invention is to provide a blood treatment filter.

Means for Solving the Problem

In order to solve the above-mentioned problem, a surface treating agent of the present invention with which a blood contact surface of a base material used for a medical device is coated is characterized with a copolymer of monomer components including:
a monomer (A) having a hydrophilic functional group of formula (1) or (2) below,
a monomer (B) having a basic functional group and
a monomer (C) having a reactive functional group
as monomer components,
wherein the copolymer has a molar ratio of the monomer (A)/(B)/(C) between 70/15/15 to 98/1/1.

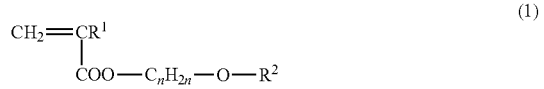

(wherein $(R^1)$s represent hydrogen or a methyl group, $R^2$ represents an alkyl group having 1 to 4 carbon atoms, n represents an integer of 2 to 4, and $R^3$ and $R^4$ independently represent hydrogen or an alkyl group having 1 to 3 carbon atoms respectively)

Preferably that the monomer (A) of formula (1) is 2-methoxyethyl (meth)acrylate or 2-ethoxyethyl (meth) acrylate and/or the monomer (A) of formula (2) is N,N-dimethyl (meth)acrylamide.

According to the above-mentioned particular structure, making use of the copolymer that comprises a monomer (A), a monomer (B) and a monomer (C) having a specified structure as monomer components, wherein the copolymer has a specified molar ratio, the monomer (A) inhibits the adhesion and activation of platelets. Further, since the monomer (C) makes the surface treating agent maintain to fix the base material, during the production and the use, the surface treating agent is prevented from detaching (eluting) from the base material. As a result, an inhibitive effect of the adhesion and activation of platelets is maintained for a long period of time. Further, when the surface treating agent is applied to a blood treatment filter, the monomers (A) and (B) of the surface treating agent simultaneously inhibit the adhesion and activation of platelets and promote selective adsorption of leukocyte.

A surface treating agent of the present invention is inclusion of the copolymer, wherein the monomer (B) having a basic functional group is at least one monomer selected from the monomers of formulae (3), (4), (5) and (6) below, respectively.

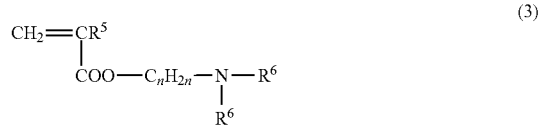

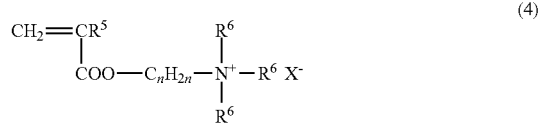

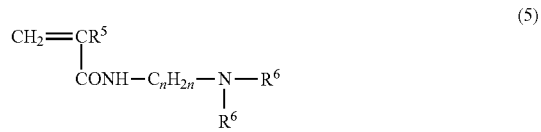

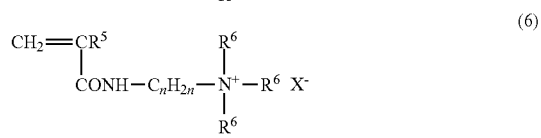

(wherein ($R^5$)s represent hydrogen or a methyl group, ($R^6$)s independently represent hydrogen or an alkyl group having 1 to 4 carbon atoms respectively, n represents an integer of 2 to 4, and ($X^-$)s represent an anion derived from halogen, sulfonic acid, sulfuric acid or the like)

It is preferred that the monomer (B) of formula (3) is N,N-dimethylaminoethyl (meth)acrylate, N,N-diethylaminoethyl (meth)acrylate, or N,N-diisopropylaminoethyl (meth)acrylate and/or the monomer (B) of formula (5) is N,N-dimethylaminopropyl (meth)acrylamide.

According to the above-mentioned construction, by constructing the monomer (B) to have a specified structure, further inhabitation of the adhesion and activation of platelets and further selective adsorption of leukocytes are achieved at the same time.

A surface treating agent of the present invention is characterized with the copolymer, wherein the monomer (C) of the copolymer having a reactive functional group is at least one monomer selected from the monomers of formulae (7) and (8) below.

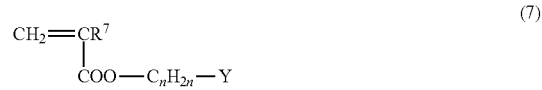

(wherein ($R^7$)s represent hydrogen or a methyl group, n represents an integer of 0 to 3, and (Y)s represent a hydroxyl group, an epoxy group, a primary amine, secondary amine or hydrogen)

It is preferred that the monomer (C) of formula (7) is 2-hydroxyethyl (meth)acrylate or glycidyl (meth)acrylate and/or the monomer (C) of formula (8) is 2-aminoethyl (meth)acrylamide.

According to the above-mentioned construction, by constructing the monomer (C) to have a specified structure, further improvement of fixation of the surface treating agent to the base material is achieved.

The filtering material for filter of the present invention has a feature that at least a part of the base material is coated with the surface treating agent. Further, it is preferred that the surface treating agent is fixed by a chemical bonding between the monomer (C) having a reactive functional group and a reactive functional group of the base material.

According to the above-mentioned construction, by constructing at least a part of the base material being coated with the surface treating agent, an effect to inhibit the adhesion and activation of platelets and an effect to adsorb leukocyte selectively are given to the filtering material. Further, since the filtering material (the base material) is maintained to be fixed preferably by the chemical bonding, the surface treating agent is prevented from detaching (eluting) from the filtering material (the base material) during the production and the use of the filtering material. As a result, the above-mentioned effects are maintained.

The blood treatment filter of the present invention is characterized with including: a housing having a blood inlet port and a blood outlet port, and a filter unit which makes interior of the housing separate into a blood inlet chamber and a blood outlet chamber, wherein at least a part of the filter unit is used for the filtering material mentioned above.

According to the above-mentioned construction, by constructing at least a part of the filter unit being used for the filtering material, an effect to inhibit the adhesion and activation of platelets and an effect to adsorb leukocyte selectively are given to the blood treatment filter. Further, since the blood treatment filter (the filter unit) is maintained to be fixed, during the production and the use of the blood treatment filter, the surface treating agent is prevented from detaching (eluting) from the filtering material for filter (the filter unit). As a result, the above-mentioned effects are maintained.

Effect of the Invention

According to the surface treating agent of the present invention, when a blood contact surface of a base material that is used for a medical device is coated with the surface treating agent, the surface treating agent not only can fix the base material effectively and can maintain an excellent antithrombotic performance, but also can show excellent leukocyte removal ability and excellent platelet collection rate when a base material of a blood treatment filter is coated with the surface treating agent. Further, according to the filtering material for filter and the blood treatment filter of the present invention, excellent antithrombotic performance is maintained, and also excellent leukocyte removal ratio and excellent platelet collection ratio are shown.

BRIEF DESCRIPTION OF THE DRAWINGS

FIG. 1 is a cross sectional view showing a structure of the blood treatment filter of the present invention.

DETAILED DESCRIPTION OF THE PREFERRED EMBODIMENT

Hereinafter, embodiments of the surface treating agent of the present invention are described in detail. The surface treating agent with which a blood contact surface of a base material used for a medical device is coated comprising a copolymer of monomer components including: a monomer (A) having a hydrophilic functional group of formula (1) or (2) below, a monomer (B) having a basic functional group and a monomer (C) having a reactive functional group, wherein the copolymer has a molar ratio of the monomer (A)/(B)/(C) between 70/15/15 to 98/1/1.

Since the copolymer has an appropriate molar ratio (a molar ratio of the monomer (A)/(B)/(C) between 70/15/15 to 98/1/1), when a blood contact surface of a base material that is used for a medical device is coated with, the base material is fixed effectively and an excellent antithrombotic performance can maintained, and also excellent leukocyte removal ability and excellent platelet collection rate can be shown when a base material of a blood treatment filter is coated with. If the molar ratio of the monomer (A) is below 70, the amount of the monomer (A) is insufficient, therefore the adhesion and activation of platelets cannot be inhibited, hence the antithrombotic performance may decrease. While if a molar ratio of the monomer (A) is above 98, the amount of the monomer (C) is insufficient, therefore the copolymer cannot be fixed to the base material effectively.

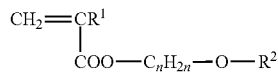
(1)

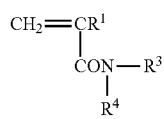
(2)

(wherein $(R^1)$s represent hydrogen or a methyl group, $R^2$ represents an alkyl group having 1 to 4 carbon atoms, n represents an integer of 2 to 4, and $R^3$ and $R^4$ independently represent hydrogen or an alkyl group having 1 to 3 carbon atoms respectively)

With respect to the monomer (A) which is a monomer component of the copolymer (the surface treating agent), a hydrophilic functional group is alkoxy group or amide group (unsubstituted amide, N-1 substituted amide, N-2 substituted amide). Further, the monomer (A) is represented by formula (1) or (2). The monomer (A) has an effect to inhibit the adhesion and activation of platelets.

The monomer (A) of the formula (1) described above includes the alkoxyalkyl (meth)acrylates which include, for example, methoxyethyl (meth)acrylate, methoxypropyl (meth)acrylate, methoxybutyl (meth)acrylate, ethoxyethyl (meth)acrylate, ethoxypropyl (meth)acrylate, ethoxybutyl (meth)acrylate, propoxyethyl (meth)acrylate, propoxypropyl (meth)acrylate, propoxybutyl (meth)acrylate, and the like. Each of them may be used by itself or a plurality thereof may be used in combination. Among the above monomers, from the viewpoints of economy and ease of manipulation, methoxyethyl (meth)acrylate or ethoxyethyl (meth)acrylate are preferred. 2-methoxyethyl (meth)acrylate or 2-ethoxyethyl (meth)acrylate are more preferred.

The monomer (A) of the formula (2) described above may be (meth)acrylamides. Besides (meth)acrylamide, for example, N-methyl (meth)acrylamide, N-ethyl (meth)acrylamide, N-propyl (meth)acrylamide, N,N-dimethyl (meth)acrylamide, N,N-diethyl (meth)acrylamide and N,N-dipropyl (meth)acrylamide. Each of them may be used by itself or a plurality thereof may be used for the monomer (A) in combination. Among the above monomers, from the viewpoints of economy and ease of manipulation, N,N-dimethyl (meth)acrylamide is preferred.

The monomer (B) having a basic functional group, which is a monomer component of the copolymer, may be any monomer which can copolymerize with the monomer (A) in a specific molar ratio. Examples of the basic functional group include amino groups (primary amines, secondary amines, tertiary amines, quaternary amines (ammonium salts)), a pyridyl group, an aziridine group and an imidazolyl group. The monomer (B) has an effect to adsorb leukocyte selectively.

It is preferred that the monomer (B) is at least one monomer selected from the monomers of formulae (3), (4), (5) and (6) below, respectively.

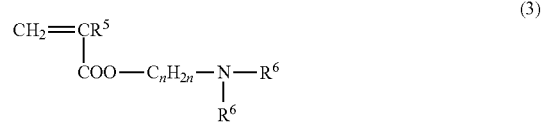
(3)

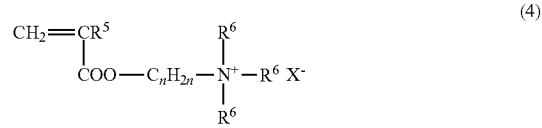
(4)

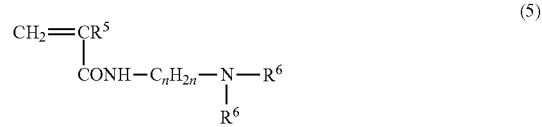
(5)

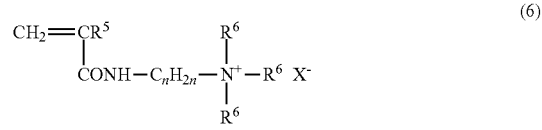
(6)

(wherein $(R^5)$s represent hydrogen or a methyl group, $(R^6)$s independently represent hydrogen or an alkyl group having 1 to 4 carbon atoms respectively, n represents an integer of 2 to 4, and $(X^-)$s represent an anion derived from halogen, sulfonic acid, sulfuric acid or the like)

The monomer (B) of the formula (3) above may be aminoalkyl (meth)acrylates. Examples thereof include, for example, aminoethyl (meth)acrylate, aminoisopropyl (meth)acrylate, amino-n-butyl (meth)acrylate, N-methylaminoethyl (meth)acrylate, N-ethylaminoisobutyl (meth)acrylate, N-isopropylaminoethyl (meth)acrylate, N-n-butylaminoethyl (meth)acrylate, N-t-butylaminoethyl (meth)acrylate, N,N-dimethylaminoethyl (meth)acrylate, N,N-dimethylaminopropyl (meth)acrylate, N,N-dimethylaminobutyl (meth)acrylate, N-methyl-N-ethylaminoethyl (meth)acrylate, N-methyl-N-butylaminoethyl (meth)acrylate, N,N-diethylaminoethyl (meth)acrylate, N,N-diethylaminopropyl (meth)acrylate, N,N-dipropylaminoethyl (meth)acrylate, N,N-dipropylaminopropyl (meth)acrylate and N,N-diaminobutylpropyl (meth)acrylate. Each of them may be used by itself or a plurality thereof may be used in combination. Among the above monomers, from the viewpoints of economy and ease of manipulation, N,N-dimethylaminoethyl (meth)acrylate, N,N-diethylaminoethyl (meth)acrylate or N,N-diisopropylaminoethyl (meth)acrylate are preferred.

The monomer of the formula (5) above may be aminoalkyl (meth)acrylamides. Examples thereof include, for example, aminoethyl (meth)acrylamide, aminoisopropyl (meth)acrylamide, amino-n-butyl (meth)acrylamide, N-methylaminoethyl (meth)acrylamide, N-ethylaminoisobutyl (meth)acrylamide, N-isopropylaminomethyl (meth)acrylamide, N-n-butylaminoethyl (meth)acrylamide, N-t-butylaminoethyl (meth)acrylamide, N,N-dimethylaminoethyl (meth)acrylamide, N,N-dimethylaminopropyl (meth)acrylamide, N,N-dimethylaminobutyl (meth)acrylamide, N-methyl-N-ethylaminoethyl (meth)acrylamide, N-methyl-N-butylaminoethyl (meth)acrylamide, N,N-diethylaminoethyl (meth)acrylamide, N,N-diethylaminopropyl (meth)acrylamide, N,N-dipropylaminoethyl (meth)acrylamide, N,N-dipropylaminopropyl (meth)acrylamide and N,N-diaminobutylpropyl (meth)acrylamide. Each of them may be used by itself or a plurality thereof may be used in combination. Among the above monomers, from the viewpoints of economy and ease of manipulation, N,N-dimethylaminopropyl (meth)acrylamide is preferred.

The monomers (B) of the formulae (4) and (6) above are each derivatives obtained by treating the monomers of the formulae (3) and (5) above respectively, with an alkyl halide, an alkyl sulfate or the like to convert them into quaternary ammonium salts.

Further, with respect to the present invention, the monomers (B), except the formulae (3) to (6) above, may include at least one monomer selected from the group consisting of aminostyrene, N,N-dimethylaminostyrene, N,N-diethylaminostyrene, vinylpyridine, N-methylvinylpyridine, N-ethylvinylpyridine, vinylquinoline, ethyleneimine, propyleneimine, N-aminoethylethyleneimine, vinylimidazole, vinylpyrazoline and vinylpyrazine. Furthermore, the monomers may be each derivatives obtained by treating the monomers described above respectively with an alkyl halide, an alkyl sulfate or the like to convert them into quaternary ammonium salts.

The monomer (C) having a reactive functional group is a monomer component of the copolymer, whatever monomer having a reactive functional group that is capable to copolymerize with the monomer (A) and (B) in a specific molar ratio may be used for a monomer component of the copolymer. The reactive functional group includes, for example, a hydroxyl group, an epoxy group, a primary amine, secondary amine or hydrogen. The monomer (C) has an effect to fix the copolymer (the surface treating agent) to the base material.

It is preferred that the monomer (C) is at least one monomer selected from the monomers of formulae (7) and (8) below.

(wherein ($R^7$)s represent hydrogen or a methyl group, n represents an integer of 0 to 3, and (Y)s represent a hydroxyl group, an epoxy group, a primary amine, secondary amine or hydrogen)

The monomer (C) of the formula (7) above may be any of, for example, hydroxyalkyl (meth)acrylate, epoxyalkyl (meth)acrylate, aminoalkyl (meth)acrylate and (meth) acrylic acid. Each of them may be used by itself or a plurality thereof may be used in combination. Among the above monomers, from the viewpoints of economy and ease of manipulation, hydroxyalkyl (meth)acrylate or epoxyalkyl (meth)acrylate are preferred. Hydroxyethyl (meth)acrylate (2-hydroxyethyl (meth)acrylate) or glycidyl (meth)acrylate are more preferred.

The monomer (C) of the formula (8) above may be any of, for example, hydroxyalkyl (meth)acrylamide, epoxyalkyl (meth)acrylamide, aminoalkyl (meth)acrylamide, (meth) acrylamide. Each of them may be used by itself or a plurality thereof may be used in combination. Among the above monomers, from the viewpoints of economy and ease of manipulation, aminoalkyl (meth)acrylamide is preferred. Aminoethyl (meth)acrylamide (2-aminoethyl (meth)acrylamide) is more preferred.

The copolymer has preferable a mass-average molecular weight of 3,000 to 300,000 and more preferably 7,000 to 50,000. If the mass-average molecular weight is less than 3,000, it is often difficult to synthesize the copolymer. On the other hand, if the mass-average molecular weight is more than 300,000, it is often difficult to dissolve the copolymer into organic solvents to coat (coating) the base material. Due to this, fixation of the copolymer to the base material tends to become difficult.

The medical device used for the present invention means a blood contact surface. Examples of the medical device include a blood treatment filter, a plasma separator, a blood bag, a blood circuit, an indwelling needle, an oxygenator, a blood reservoir, a dialyzer, a catheter, a guide wire, a stent, an artificial blood vessel, a coalescence preventing material, a wound covering material, and the like. The surface treating agent (the copolymer) of the present invention is preferably used for a blood treatment filter, specifically, for a filtering material that is used for a blood treatment filter (a leukocyte removing filter of platelet passage-type).

Hereinafter, the filtering material of the present invention will be described. The filtering material has a feature to have a base material at least a part of which or a blood contact portion therein is coated with the surface treating agent mentioned above.

The base material may be in the form of a sponge-like porous material (a three dimensionally networked continuously porous material), a nonwoven fabric, a woven fabric, a knitted fabric and the like. Among them, a sponge-like porous material or a nonwoven fabric is preferred. In the case of a sponge-like porous material, a mean pore diameter measured using a perm porosimeter of 1 to 20 μm is preferred. If the mean pore diameter is below 1 μm, the filter material tends to be clogged while if it is above 20 μm, the performance (the removal ratio of leukocyte) as the filtering material for filter (blood treatment filter) may sometimes decrease.

The material of the base material may be, for example, any of synthetic polymers such as polyester (polyethylene terephthalate, polybutylene terephthalate), polyolefin, halogenated polyolefin, polyurethane, polyamide, polysulfone, polyethersulfone, and mixtures thereof.

The method for coating the base material with the surface treating agent includes such known methods as a coating method; a method using graft polymerization with radiation, electron beam or ultraviolet ray; and a method using a chemical reaction with a functional group of the base material.

As the filtering material has the base material coated with the surface treating agent, it is preferable that the surface treating agent on the base material is fixed by a chemical bonding between a monomer (C) of the surface treating agent and a reactive functional group of the base material. The functional group of the base material includes an epoxy group, a carboxy group, a hydroxyl group and the like. Further, a base material itself which has the reactive functional group may be selected, or the reactive functional group may be introduced into a base material using such as graft polymerization.

BRIEF DESCRIPTION OF THE FIGURE

Hereinafter, the blood treatment filter of the present invention will be described in detail. As shown in FIG. 1, the blood treatment filter 1 includes: a housing 2 having a blood inlet port 4 and a blood outlet port 6, and a filter unit 7 which disposes to separate the inner space of the housing 2 separate into a blood inlet chamber 8 and a blood outlet chamber 9, wherein at least a part of the filter unit is used for the filtering material mentioned above.

The housing 2 includes: a cover 3 having one end where a blood inlet port 4 is formed, through which blood is introduced is formed; and a bottom 5 having one end is made to flow out, where a blood outlet port 6 through which the blood treated by the filter unit 7. A periphery of the filter unit 7 is sandwiched between the cover 3 and the bottom 5. Hereon, the contact portions are fusion-bonded by high frequency fusion or ultrasonic fusion. Thereby, the inner space of the housing 2 is separated into the blood inlet chamber 8 communicating with the blood inlet port 4 and the blood outlet chamber 9 communicating with the blood outlet port 6. Further, the material of the housing 2 may be, for example, any of polycarbonate, polyvinyl chloride, ethylene-vinyl acetate copolymer, ABS resin, polyolefin and the like.

The blood treatment filter 1 has such a structure that the introduced blood flows from the blood inlet port 4 into the housing 2, then via the blood inlet chamber 8, passes through the filter unit 7, flows into the blood outlet chamber 9 and finally flows out of the housing 2 from the blood outlet port 6.

The filter unit 7 includes a main filter unit 7b and a pre-filter unit 7a which is attached on the up-stream side of the main filter unit 7b. The main filter unit 7b removes leukocytes from the introduced blood. The pre-filter unit 7a has a larger mean pore diameter than the main filter unit 7b. Incoming blood easily enters the pre-filter unit 7a before the main filter unit 7b, and the pre-filter unit 7a hardly removes leukocytes. In addition, aggregates could be formed in the blood by aggregation of proteins and blood components. Therefore, pre-filer unit 7a also has a role to remove the aggregates to inhibit or to prevent the aggregates from clogging the main filter unit 7b.

At least a part of the filter unit 7 being made of the filtering material mentioned above means specifically that the copolymer (the surface treating agent) coats (fixes) only the main filter unit 7b. Preferably, the main filter unit 7b has a multi-layer structure to improve leukocyte removal ability.

When the main filter unit 7b is made of such a base material as a sponge-like porous membrane of polyurethane, this base material functions as a filtering material. The base material is capable of capturing leukocyte selectively (leukocyte removal property) and passing platelet and erythrocyte (platelet collection property and erythrocyte collection property). In this case, it is preferred that only a downstream layer of the main filter unit 7b is coated (fixed) with the copolymer (the surface treating agent), thus an capability to capture leukocyte selectively is added to the downstream layer in order to improve the leukocyte removal property of the downstream layer better than that of the upstream layer, and to maintain the ability to pass platelet and erythrocyte. Then, it is possible to obtain the same effect with a smaller number of the stacked treated base material layers than a larger number of the untreated base material layers. Thereby, the smaller number of the layer reduces the residual platelet and erythrocyte in the base material. Therefore, it is possible to improve a platelet collection rate and an erythrocyte collection rate.

If the main filter unit 7b is made of a base material, for example, such as a nonwoven fabric of polyester, which itself has its own ability to capture leukocyte and platelet (leukocyte removal property), and, the ability to pass erythrocyte (erythrocyte collection property), it is preferred that all layers of the main filter unit 7b is coated (fixed) with the copolymer (the surface treating agent). Thereby, an ability to pass platelet is added, and, an ability to capture leukocyte is to be maintained or improved.

Further, with respect to the main filter unit 7b, the amount of fixed copolymer (the surface treating agent) on the main filter unit 7b may be increased toward downstream side (along with the blood flow direction).

Further, in the present invention, the configuration of the filter unit 7 is not limited to the combination of the main filter unit 7b and pre-filter 7a. The configuration made of the main filter unit 7b alone may satisfy the present invention.

The blood treatment filter 1 (the filter unit 7) removes leukocytes selectively from the blood (such as the whole blood) flowing therethrough and passes platelets, erythrocytes and plasma. Therefore, a blood bag system equipped with the blood treatment filter 1 collects the blood free of leukocytes. Moreover, a blood product free of leukocytes is produced by separating each of blood cell components that is separated from the filtered blood which causes little or no side effect due to leukocytes.

EXAMPLES

Hereinafter, the present invention will be described in detail by examples. However, the present invention is not limited thereto. Examples 1 to 8 and Comparative Examples 1 to 5 relate to preparation of surface treating agents. Test Examples 1 to 7 relate to evaluation of performances (amount of fixation, blood filtration property and antithrombotic performance) of surface treating agents.

(1) Preparation of the Surface Treating Agents

Example 1

32.7 g of 2-methoxyethyl acrylate (MEA; produced by Wako Pure Chemical Industries, Ltd.), 2.2 g of N,N-dimethylaminoethyl methacrylate (DMAEMA; produced by Wako Pure Chemical Industries, Ltd.) and 1.8 g of 2-hydroxyethyl methacrylate (HEMA; produced by Wako Pure Chemical Industries Ltd.) were dissolved in 145.0 g of anhydrous dimethylformamide (DMF; produced by Wako Pure Chemical Industries Ltd.). After having nitrogen flow in this solution for 1 hour, 1 mL of DMF solution of 37 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was dispensed into the solution by stirring, then, the solution was dispensed by drops into n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was MEA/DMAEMA/HEMA=90/5/5. The mass average molecular weight was 32,000.

Example 2

28.7 g of N,N-dimethyl acrylamide (DMAA; produced by Wako Pure Chemical Industries, Ltd.), 1.5 g of N,N-dimethylaminoethyl methacrylate (DMAEMA; produced by Wako Pure Chemical Industries, Ltd.) and 2.0 g of 2-hydroxyethyl methacrylate (HEMA; produced by Wako Pure Chemical Industries Ltd.) were dissolved in 140.0 g of anhydrous dimethylformamide (DMF; produced by Wako Pure Chemical Industries Ltd.). After having nitrogen flow in this solution for 1 hour, 1 mL of DMF solution of 34 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was dispensed into the solution by stirring, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under a reduced pressure over a whole day to obtain a surface treating agent. The composition (molar ratio of monomer components) of the obtained polymer was determined by $^1$H-NMR. The molar ratio of monomers was DMAA/DMAEMA/HEMA=92/3/5. The mass average molecular weight was 44,000.

Example 3

39.0 g of 2-methoxyethyl acrylate (MEA; produced by Wako Pure Chemical Industries, Ltd.), 0.6 g of N,N-diethylaminoethyl methacrylate (DEAEMA; produced by Wako Pure Chemical Industries, Ltd.) and 0.4 g of 2-hydroxyethyl methacrylate (HEMA; produced by Wako Pure Chemical Industries Ltd.) were dissolved in 160.0 g of anhydrous dimethylformamide (DMF; produced by Wako Pure Chemical Industries Ltd.). After having nitrogen flow in this solution for 1 hour, 1 mL of DMF solution of 40 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was dispensed into the solution by stirring, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was MEA/DEAEMA/HEMA=98/1/1. The mass average molecular weight was 38,000.

Example 4

15.0 g of N,N-dimethyl acrylamide (DMAA; produced by Wako Pure Chemical Industries, Ltd.), 5.5 g of N,N-dimethylaminopropyl methacrylamide (DMAPMAm; produced by Wako Pure Chemical Industries, Ltd.) and 4.2 g of 2-hydroxyethyl methacrylate (HEMA; produced by Wako Pure Chemical Industries Ltd.) were dissolved in 100.0 g of anhydrous dimethylformamide (DMF; produced by Wako Pure Chemical Industries Ltd.). After having nitrogen flow in this solution for 1 hour, 1 mL of DMF solution of 25 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 80 mL of acetone (produced by Kokusan Chemical Co., Ltd.) was dispensed into the solution by stirring, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was DMAA/DMAPMAm/HEMA=70/15/15. The mass average molecular weight was 28,000.

Example 5

23.0 g of 2-ethoxyethyl methacrylate (EEMA; produced by Wako Pure Chemical Industries, Ltd.), 3.6 g of N,N-dimethylaminoethyl methacrylate (DMAEMA; produced by Wako Pure Chemical Industries, Ltd.) and 3.3 g of 2-hydroxyethyl methacrylate (HEMA; produced by Wako Pure Chemical Industries Ltd.) were dissolved in 120.0 g of anhydrous dimethylformamide (DMF; produced by Wako Pure Chemical Industries Ltd.). After having nitrogen flow in this solution for 1 hour, 1 mL of DMF solution of 30 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was EEMA/DMAEMA/HEMA=76/12/12. The mass average molecular weight was 18,000.

Example 6

27.0 g of 2-methoxyethyl acrylate (MEA; produced by Wako Pure Chemical Industries, Ltd.), 5.0 g of N,N-diisopropylaminoethyl methacrylate (DiPAEMA; produced by Wako Pure Chemical Industries, Ltd.) and 1.0 g of 2-hydroxyethyl methacrylate (HEMA; produced by Wako Pure Chemical Industries Ltd.) were dissolved in 130.0 g of anhydrous dimethylformamide (DMF; produced by Wako Pure Chemical Industries Ltd.). After having nitrogen flow in this solution for 1 hour, 1 mL of DMF solution of 33 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was MEA/DiPAEMA/HEMA=87/10/3. The mass average molecular weight was 27,000.

Example 7

Synthesis of 2-Aminoethyl Acrylamide (AEAAm) Hydrochloride 5.0 g of N-(t-butoxycarbonyl)-1,2-diaminoethane (produced by Tokyo Chemical Industry Co., Ltd.) was dissolved in 100 mL of anhydrous chloroform (produced by Wako Pure Chemical Industries Ltd.), and 5.0 g of triethylamine (produced by Wako Pure Chemical Industries Ltd.) was added to the solution. With the solution kept cooled in an ice bath, 2.5 g of acryloyl chloride (produced by Wako Pure Chemical Industries Ltd.) was added dropwise to the solution with stirring. After the addition, stirring was kept for another 30 minutes, then the chloroform layer was rinsed with 20 mL×3 times of 1 N hydrochloric acid and further with 20 mL×3 times of saturated sodium bicarbonate aqueous solution. Then, the chloroform layer was desiccated over anhydrous sodium sulfate, and was evaporated to dryness. Subsequently after the removal of the N-(t-butoxycarbonyl) protective group with 2.5 mL of 37 mass % hydrochloric acid, the residue was freeze-dried. The obtained product was determined by $^1$H-NMR. The product was found to be 2-aminoethyl acrylamide hydrochloride, and the yield was 3.2 g (77%)

Synthesis of Polymer Having 2-Aminoethyl Acrylamide (AEAAm) as a Reactive Functional Group 25.0 g of 2-methoxyethyl acrylate (MEA; produced by Wako Pure Chemical Industries, Ltd.), 1.5 g of N,N-dimethylaminoethyl acrylate (DMAEA; produced by Wako Pure Chemical Industries, Ltd.) and 1.6 g of 2-aminoethyl acrylamide (AEAAm) chloride synthesized above were dissolved in 110.0 g of anhydrous dimethylformamide (DMF; produced by Wako Pure Chemical Industries Ltd.). After having nitrogen flow in this solution for 1 hour, 1 mL of DMF solution of 28 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 80 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was MEA/DMAEA/AEAAm=90/5/5. The mass average molecular weight was 26,000.

Example 8

22.0 g of N,N-dimethyl acrylamide (DMAA; produced by Wako Pure Chemical Industries, Ltd.), 2.0 g of N,N-dimethylaminoethyl methacrylate (DMAEMA; produced by Wako Pure Chemical Industries, Ltd.) and 1.8 g of glycidyl methacrylate (GMA; produced by Wako Pure Chemical Industries, Ltd.) were dissolved in 100.0 g of anhydrous dimethylformamide (DMF; produced by Wako Pure Chemical Industries Ltd.). After having nitrogen flow in this solution for 1 hour, 1 mL of DMF solution of 26 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was DMAA/DMAEMA/GMA=90/5/5. The mass average molecular weight was 41,000.

Comparative Example 1

31.0 g of 2-methoxyethyl acrylate (MEA; produced by Wako Pure Chemical Industries, Ltd.), 2.0 g of N,N-dimethyaminoethyl methacrylate (DMAEMA; produced by Wako Pure Chemical Industries, Ltd.) and were dissolved in 130.0 g of anhydrous dimethylformamide (DMF; produced by Wako Pure Chemical Industries Ltd.). After having nitrogen flow in this solution for 1 hour, 1 mL of DMF solution of 34 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was MEA/DMAEMA=95/5. The mass average molecular weight was 52,000.

Comparative Example 2

30.0 g of N,N-dimethyl acrylamide (DMAA; produced by Wako Pure Chemical Industries, Ltd.), 2.5 g of N,N-dimethyaminoethyl methacrylate (DMAEMA; produced by Wako Pure Chemical Industries, Ltd.) and were dissolved in 130.0 g of anhydrous dimethylformamide (DMF; produced by Wako Pure Chemical Industries Ltd.). After having nitrogen flow in this solution for 1 hour, 1 mL of DMF solution of 33 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was DMAA/DMAEMA=95/5. The mass average molecular weight was 49,000.

Comparative Example 3

30.0 g of 2-methoxyethyl acrylate (MEA; produced by Wako Pure Chemical Industries, Ltd.) and 1.5 g of 2-hydroxyethyl methacrylate (HEMA; produced by Wako Pure Chemical Industries, Ltd.) were dissolved in 125.0 g of anhydrous dimethylformamide (DMF; produced by Wako Pure Chemical Industries Ltd.). After having nitrogen flow in this solution for 1 hour, 1 mL of DMF solution of 32 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was MEA/HEMA=95/5. The mass average molecular weight was 77,000.

Comparative Example 4

20.0 g of N,N-dimethyl acrylamide (DMAA; produced by Wako Pure Chemical Industries, Ltd.), 13.0 g of N,N-dimethyaminoethyl methacrylate (DMAEMA; produced by Wako Pure Chemical Industries, Ltd.) and 2.0 g of 2-hydroxyethyl methacrylate (HEMA; produced by Wako Pure Chemical Industries Ltd.) were dissolved in 125.0 g of anhydrous dimethylformamide (DMF; produced by Wako Pure Chemical Industries Ltd.). After having nitrogen flow in this solution for 1 hour, 1 mL of DMF solution of 36 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 100 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was DMAA/DMAEMA/HEMA=67/28/5. The mass average molecular weight was 43,000.

Comparative Example 5

1.5 g of N,N-diethyaminoethyl methacrylate (DEAEMA; produced by Wako Pure Chemical Industries, Ltd.) and 20.0 g of 2-hydroxyethyl methacrylate (HEMA; produced by Wako Pure Chemical Industries, Ltd.) were dissolved in 80.0 g of anhydrous dimethylformamide (DMF; produced by Wako Pure Chemical Industries Ltd.). After having nitrogen flow in this solution for 1 hour, 1 mL of DMF solution of 22 mg of 2,2'-azobisisobutyronitrile (AIBIN; produced by Wako Pure Chemical Industries, Ltd.) was added to the solution, and the solution was allowed to polymerize at 80° C. for 8 hours. After completion of the polymerization, 60 mL of acetone (produced by Kokusan Chemical Co., Ltd.) was added with stirring to the solution, then, the solution was added dropwise to n-hexane (produced by Kokusan Chemical Co., Ltd.) to form precipitates and the product was isolated. The isolated product was dissolved in acetone and the resulting solution was added dropwise to n-hexane to form precipitates and thus purified totally three times. The purified product was dried under reduced pressure over a whole day to obtain a surface treating agent. The composition (molar ratio of monomer components) of the obtained polymer was determined by $^1$H-NMR. The molar ratio of monomers was DEAEMA/HEMA=5/95. The mass average molecular weight was 66,000.

(2) Evaluation of Performance of Various Surface Treating Agents

Test Example 1

Amount of Fixation of Various Surface Treating Agents (Except Example 8)

Preparation of GMA-Grafted PU Membrane 21 cm×25 cm of a polyurethane sponge-like porous membrane that is as thick as 1.2 mm (PU: E394 POTA, produced by Nippon Miractran Co., Ltd.; mean pore diameter: 5.0 μm, porosity: 85%) was exposed for 30 seconds to plasma of argon flux of 25 Pa with an output of 200 W. Then, the pressure of argon flow was decreased to 0.5 Pa. After decreasing the argon pressure, previously deaerated glycidyl methacrylate (GMA; produced by Wako Pure Chemical Industries, Ltd.) was introduced under a negative pressure and was graft polymerized at 56 Pa for 3 minutes. Residual GMA monomer in the reaction system was evacuated with a vacuum pomp for 3 minutes. Then, the system was returned to the atmospheric pressure, and thus GMA-grafted PU membrane was obtained.

Fixation of the Surface Treating Agents

Using each of the solvents indicated in Table 1, 450 g of a solution was prepared in 500 mL beaker, which contained a final concentration of 0.5 mass % of each of the surface treating agents synthesized in Examples 1 to 6 and Comparative Examples 1 to 5 and a final concentration of 0.25 mass % of pyridine (produced by Wako Pure Chemical Industries, Ltd.). 450 g of a solution was prepared in 500 mL beaker, which contained a final concentration of 0.5 mass % of the surface treating agent of Example 7 without adding pyridine into a mixed solution of water and methanol where methanol/water=1/1 (by mass ratio).

Into each of the solutions of the above surface treating agents, the GMA-grafted membranes, in order to be immersed completely in the solutions in 500 mL beaker, were cut into 3 sheets of 7 cm×25 cm respectively. And all the 3 sheets were placed into each of the beakers and were synthesized by stirring in constant temperature water bath at 65° C. for 8 hours. Thus, the various surface treating agents (except Example 8) were fixed to the grafted membranes.

Washing of the Membranes Fixed with the Surface Treating Agents

One sheet out of 3 sheets of the membranes fixed with the various surface treating agents was dried continuously in the same draft chamber after the fixation and further heated in an oven at 80° C. for 8 hours. Each of the other 2 sheets was washed by showering with RO water at 60° C. for 8 hours, and was washed by Soxhlet extraction-washing with methanol as solvent for 8 hours. Then, the washed sheet was dried in a draft chamber overnight and further dried in an oven at 80° C. for 4 hours.

Amount of Fixation of Unwashed or Washed Samples

The dried membranes fixed with the various surface treating agents were investigated by Trypan Blue staining method. That is, the resulting membranes were punched to obtain disks of Φ 26 mm in diameter. Then, the disk was mounted in a holder made of PP (produced by Advantech Co., Ltd.). The holder was filled with RO water. Here, a concentration-adjusted of aqueous solution of Trypan Blue (produced by Merck KGaA) was prepared to be absorbed in the range of 1.15±0.05 at the maximum absorption wavelength. The concentration-adjusted aqueous solution of Trypan Blue was fed at 15 mL/min for 90 seconds. After the feeding, 50 mL of RO water was fed to wash excessive Trypan Blue. The membrane was taken out of the holder and was dried in an oven at 80° C. Then, the reflection absorption of 599 nm was measured using Chromatoscanner CS-930 (producted by Shimadzu Corporation). The results obtained are shown in Table 1.

Test Example 2

Amount of Fixation of Surface Treating Agent of Example 8

Preparation of AA-Grafted PU Membrane 21 cm×25 cm of a polyurethane sponge-like porous membrane that is as thick as 1.2 mm (PU: E394 POTA, produced by Nippon Miractran Co., Ltd.; mean pore diameter: 5.0 μm, porosity: 85%) was exposed for 30 seconds to plasma of argon flux of 25 Pa with an output of 200 W. Then, the pressure of argon flow was decreased to 0.5 Pa. After decreasing the argon pressure, previously deaerated acrylic acid (AA; produced by Wako Pure Chemical Industries, Ltd.) was introduced under negative pressure and was graft polymerized at 37 Pa for 5 minutes. Residual AA monomer in the reaction system was evacuated with a vacuum pomp for 3 minutes. Then, the system was returned to atmospheric pressure, and thus AA-grafted PU membrane was obtained.

Fixation of the Surface Treating Agent 450 mL of an aqueous solution was prepared, which contained each of final concentrations of 10 mM of ethylenediamine (EDA: produced by Wako Pure Chemical Industries, Ltd.) and dehydration-condensation agent DMT-MM (produced by Kokusan Chemical Co., Ltd.) respectively. The solution was poured gently into 500 mL beaker in which the AA-grafted membrane that was cut into 3 sheets of 7 cm×25 cm was placed. And the sheets were reacted at room temperature for 6 hours continuously in the same beaker. After completion of the reaction, the membrane was washed by RO water for 3 hours, and was dried in an oven at 80° C. for 4 hours. The solution of the surface treating agent of Example 8 was prepared in a mixed solution of water and methanol where methanol/water=1/1 (by mass ratio) to a final concentration of 0.5 mass %. The solution was prepared in 500 mL beaker to obtain 450 g. The 3 sheets of surface aminationed AA-grafted membranes were placed into the beaker and were stirred in constant temperature water bath at 65° C. for 8 hours. Thus, the surface treating agent of Example 8 was fixed to the grafted membrane.

Washing of the Membranes Fixed with the Surface Treating Agent

Samples were prepared in the same manner as in Test Example 1.

Amount of Fixation of Unwashed or Washed Samples

Samples were prepared in the same manner as in Test Example 1. The results obtained are shown in Table 1.

TABLE 1

| surface treating agent | Composition of surface treating agent (mol %) | Solvent for fixation (by mass rtio) | Amount of fixation | | |
|---|---|---|---|---|---|
| | | | unwashed | washed by RO water | washed by methanol |
| Example 1 | MEA/DMAEMA/HEMA = 90/5/5 | water/methanol = 1/1 | 0.48 | 0.40 | 0.35 |
| Example 2 | DMAA/DMAEMA/HEMA = 92/3/5 | water | 0.40 | 0.32 | 0.32 |
| Example 3 | MEA/DEAEMA/HEMA = 98/1/1 | water/methanol = 1/1 | 0.36 | 0.32 | 0.28 |
| Example 4 | DMAA/DMAPMAm/HEMA = 70/15/15 | water | 0.60 | 0.52 | 0.51 |
| Example 5 | EEMA/DMAEMA/HEMA = 76/12/12 | water/methanol = 1/1 | 0.52 | 0.50 | 0.47 |
| Example 6 | MEA/DiPAEMA/HEMA = 87/10/3 | water/methanol = 1/1 | 0.49 | 0.43 | 0.40 |
| Example 7 | MEA/DMAEA/AEAAm = 90/5/5 | water/methanol = 1/1 | 0.47 | 0.40 | 0.38 |
| Example 8 | DMAA/DMAEMA/GMA = 90/5/5 | water/methanol = 1/1 | 0.36 | 0.28 | 0.26 |
| Comparative Example 1 | MEA/DMAEMA = 95/5 | water/methanol = 1/1 | 0.51 | 0.42 | 0.03 |
| Comparative Example 2 | DMAA/DMAEMA = 95/5 | water | 0.49 | 0.02 | 0.00 |
| Comparative Example 3 | MEA/HEMA = 95/5 | water/methanol = 1/1 | 0.00 | 0.00 | 0.00 |
| Comparative Example 4 | DMAA/DMAEMA/HEMA = 67/28/5 | water | 0.87 | 0.75 | 0.72 |
| Comparative Example 5 | DEAEMA/HEMA = 5/95 | water/methanol = 1/1 | 0.55 | 0.46 | 0.45 |

From Table 1, with respect to such polyurethane sponge-like porous membranes (PU porous membranes) treated with the surface treating agents which were obtained in Examples 1 to 8 and Comparative Examples 4 and 5, that includes a monomer (B) having a basic functional group and a monomer (C) having a reactive functional group at the same time, it is apparent that the membranes were strongly stained by Trypan Blue even after the RO water-washing or the Soxhlet extraction-washing with methanol as solvent. It showed that the surface treating agents having a basic functional group were fixed on the PU porous membranes. On the other hand, with respect to such PU porous membranes treated with the surface treating agents which were obtained in Comparative Examples 1 and 2, that includes monomer (B) having a basic functional group but no monomer (C) having a reactive functional group, and the surface treating agents which were obtained in Comparative Example 3 that includes no monomer (B), it is shown that the surface treating agents were washed away from the membranes, using solvents that solve the surface treating agents. The membranes were hardly stained or not stained at all by Trypan Blue.

Test Example 3

Blood Filtration Property of Surface Treating Agents Fixed to PU Sponge-Like Porous Membrane In Test Example 1, the PU porous membranes Soxhlet extraction-washed with methanol of Examples 1 to 8 and Comparative Examples 3 to 5, and the unwashed PU porous membranes of Comparative Examples 1 and 2 were punched to obtain disks of Φ 26 mm in diameter. The obtained one disk was assembled into a blood circuit which was used as a sample of blood filtration property test. Blood collected from healthy volunteers as whole blood with CPD which was stored at 22° C. for 24 hours was used. Each of the samples was filtrated in an amount of 45 mL. Further, expressed as Comparative Example 6, an untreated PU porous membrane to which the surface treating agent was not fixed was also subjected to the filtration and evaluated in the same manner. Concentration of leucocytes and concentration of platelets before and after filtration were calculated using automatic blood cell counter (Sysmex XE2100, produced by Toa Medical Electronics (Sysmex Corporation)). Leukocyte removal rate and platelet collection ratio was calculated respectively according to the following equation. The results obtained are shown in Table 2.

Leukocyte removal ratio (%)=(1−(number of leukocytes after filtration)/(number of leukocytes before filtration))*100

Platelet collection ratio (%)=((number of platelets after filtration)/(number of platelets before filtration))*100

TABLE 2

| surface treating agent | Composition of surface treating agent (mol %) | Leukocyte removal ratio (%) | Platelet collection ratio (%) | note |
|---|---|---|---|---|
| Example 1 | MEA/DMAEMA/HEMA = 90/5/5 | 94.8 | 95.8 | Soxhlet extraction-washed |
| Example 2 | DMAA/DMAEMA/HEMA = 92/3/5 | 95.3 | 95.6 | Soxhlet extraction-washed |
| Example 3 | MEA/DEAEMA/HEMA = 98/1/1 | 93.3 | 96.2 | Soxhlet extraction-washed |
| Example 4 | DMAA/DMAPMAm/HEMA = 70/15/15 | 97.2 | 94.8 | Soxhlet extraction-washed |
| Example 5 | EEMA/DMAEMA/HEMA = 76/12/12 | 95.2 | 94.9 | Soxhlet extraction-washed |

TABLE 2-continued

| surface treating agent | Composition of surface treating agent (mol %) | Leukocyte removal ratio (%) | Platelet collection ratio (%) | note |
|---|---|---|---|---|
| Example 6 | MEA/DiPAEMA/HEMA = 87/10/3 | 96.6 | 95.0 | Soxhlet extraction-washed |
| Example 7 | MEA/DMAEA/AEAAm = 90/5/5 | 94.4 | 95.3 | Soxhlet extraction-washed |
| Example 8 | DMAA/DMAEMA/GMA = 90/5/5 | 93.3 | 95.1 | Soxhlet extraction-washed |
| Comparative Example 1 | MEA/DMAEMA = 95/5 | 89.9 | 95.7 | Unwashed |
| Comparative Example 2 | DMAA/DMAEMA = 95/5 | 70.2 | 95.2 | Unwashed |
| Comparative Example 3 | MEA/HEMA = 95/5 | 60.3 | 97.0 | Soxhlet extraction-washed |
| Comparative Example 4 | DMAA/DMAEMA/HEMA = 67/28/5 | 99.8 | 20.2 | Soxhlet extraction-washed |
| Comparative Example 5 | DEAEMA/HEMA = 5/95 | 73.1 | 78.9 | Soxhlet extraction-washed |
| Comparative Example 6 | Untreated PU porous membrane | 65.9 | 95.1 | Unwashed |

From Table 2, it is apparent that the PU porous membranes fixed with the surface treating agents obtained in Examples 1 to 8 showed a tremendously improvement in leukocyte removal ratio with a preservation of platelet collection ratio in comparison to the PU porous membranes fixed with the surface treating agents obtained in Comparative Examples 1 to 5 and untreated PU porous membrane of Comparative Example 6. On the other hand, the PU porous membranes treated with the surface treating agents obtained in Comparative Examples 1 and 2 which cannot be fixed to the membranes, showed a poorer leukocyte removal ratio in comparison to any of Examples 1 to 8, probably because the surface treating agents were washed away into blood. Further, the surface treating agents obtained in Comparative Example 3 lowered the leukocyte removal ratio in comparison to the untreated membrane (Comparative Example 6).

The surface treating agents obtained in Comparative Example 4 having a lot of basic functional groups gave a big decrease in the leukocyte removal ratio in comparison to the untreated membrane. While, in Comparative Example 5, an improved leukocyte removal ratio was obtained in comparison to the untreated membrane but the leukocyte removal ratio fell short of any surface treating agent of Examples 1 to 8, further the platelet collection ratio was apparently decreased.

Test Example 4

Blood Filtration Property of Surface Treating Agents Fixed to Nonwoven Fabric of Polyester The same procedures were repeated as in Example 1 except that nonwoven fabrics of polypropylene (PP nonwoven fabrics) having an average fiber diameter of 2.1 μm, a basis weight of 31 g/m² and a thickness of 0.20 mm were used. That is, the surface treating agents of Examples 1 and 2 were fixed to the fabrics, and the fabrics were Soxhlet extraction-washed with methanol. Thus, PP nonwoven fabrics fixed with two kinds of surface treating agents were obtained. Each of the PP nonwoven fabrics fixed with the surface treating agents were punched to obtain disks of Φ 26 mm in diameter. The obtained 6 disks were assembled into a blood circuit which was used as a sample of blood filtration property test. Further, expressed as Comparative Example 7, a PP nonwoven fabrics to which the surface treating agent was not fixed at all and expressed as Comparative Example 8, a PP nonwoven fabric onto which 0.2% of Decaglyn (a surfactant: produced by Nikko Chemicals Co., Ltd.) was simply coated were also assembled into a blood circuit each of which was used as a sample of blood filtration property test in the same manner. The same procedures were repeated as in Test Example 3. That is, blood collected from healthy volunteers as whole blood with CPD which was stored at 22° C. for 24 hours was used. Each of the samples was filtrated in an amount of 45 mL. Leukocyte removal rate and platelet collection ratio was calculated respectively. The results obtained are shown in Table 3.

TABLE 3

| surface treating agent | Composition of surface treating agent (mol %) | Leukocyte removal ratio (%) | Platelet collection ratio (%) | note |
|---|---|---|---|---|
| Example 1 | MEA/DMAEMA/HEMA = 90/5/5 | 92.7 | 91.9 | |
| Example 2 | DMAA/DMAEMA/HEMA = 92/3/5 | 91.4 | 92.8 | |
| Comparative Example 7 | Untreated PP nonwoven fabric | — | — | not infiltrated |
| Comparative Example 8 | Surfactant coated PP nonwoven fabric | 60.0 | 67.7 | |

From Table 3, it is apparent that with regard to untreated PP nonwoven fabric in Comparative Example 7, blood could not be infiltrated into the fabric and hence blood could not be filtered, while, the PP nonwoven fabric fixed with the surface treating agents obtained in Examples 1 and 2 not only showed an improved hydrophilicity and enabled filtration, but also showed a great improvement in leukocyte removal ratio and platelet collection ratio in comparison to the surfactant coated PP nonwoven fabric in Comparative Example 8.

Test Example 5

Blood Filtration Property of Mockup Configuration

A punched disk of Φ 30 mm in diameter of untreated PU porous membrane having mean pore diameter of 6.0 μm for pre-filter unit, two disks of membrane having mean pore diameter of 4.0 μm for main filter unit and a disk of membrane (mean pore diameter of 5.0 μm) fixed with the surface treating agent of Example 1, 4 disks in total were assembled into a filtration module in this order which was used as a mockup configurational sample.

Blood filtration evaluation was carried out using blood collected from healthy volunteers as whole blood with CPD which was stored at 22° C. for 1 hour was filtrated in an amount of 60 mL. In this blood filtration evaluation blood was filtered made to pass from the untreated membrane side. Concentrations of platelets and concentrations of erythrocytes before and after filtration were calculated respectively using automatic blood cell counter (Sysmex XE2100, produced by Toa Medical Electronics (Sysmex Corporation)). Leaked leukocyte number was calculated using flowcytometer (EPICS XL; produced by Beckman Coulter, Inc.). The results obtained are shown in Table 4.

In addition, instead of the membrane fixed with the surface treating agent of Example 1, a disk of membrane fixed with the surface treating agent of Example 2 was assembled into the filtration module made of 4 disks in total, the same evaluation procedures were repeated as above-mentioned. The results obtained are shown in Table 4.

Further, expressed as Comparative Example 9, instead of the membrane fixed with the surface treating agent of Example 1, a disk of membrane having mean pore diameter of 5.0 µm without the surface treating agent fixed was assembled into the filtration module made of 4 disks in total, the same evaluation procedures were repeated as above-mentioned. Furthermore, expressed as Comparative Example 10, instead of the membrane fixed with the surface treating agent of Example 1, 4 disks of membranes having mean pore diameter of 4.0 µm were assembled into the filtration module made of 6 disks in total, the same evaluation procedures were repeated as above-mentioned. The results obtained are shown in Table 4.

removal ratio, it increases the amount of residual platelets and erythrocytes in the filtering material, the platelet collection rate and the erythrocyte collection rate decrease; in contrast, by assembling the membrane fixed with the surface treating agents of the present invention (Examples 1 and 2) which have excellent leukocyte adsorbability and enables a smaller number of disks to improve leukocyte removal ratio tremendously. Thus, a leukocyte removing filter having an improved platelet collection property can be provided.

Test Example 6

Evaluation of Antithrombotic Performance of Surface Treating Agents

Under the same condition instead of the PU porous membranes of Examples 1 and 2, 0.1 mm thickness of polyurethane sheets (PU: E394 POTA, produced by Nippon Miractran Co., Ltd.) was used, the sheets were fixed with the surface treating agents of Examples 1 to 8 and Comparative Examples 1 to 5. Each of the fixed sheets was washed by Soxhlet extraction-washing with methanol as solvent for 8 hours. And then, each sheet was dried in an oven at 80° C. for 4 hours. Thus, expressed as Comparative Example 11, an untreated PU sheet to which the surface treating agent was not fixed was prepared.

Under the same condition instead of the PU sheet, 0.1 mm thickness of polypropylene sheet (PP: produced by Sumitomo Chemical Co., Ltd.) and polyethylene terephthalate sheet (PET: produced by Teijin DuPont Films Japan Limited) were used, the sheets were fixed, washed and dried. Further, expressed as Comparative Examples 12 and 13, an

TABLE 4

| surface treating agent | Structure of membrane | Leaked Leukocyte number (cell/unit) | Platelet collection ratio (%) | Erythrocyte collection ratio (%) |
|---|---|---|---|---|
| Example 1 | Pre-filter unit: 1 disk of membrane having mean pore diameter (untreated) of 6 µm<br>Main filter unit (Up-stream): 2 disks of membranes having mean pore diameter of 4 µm (untreated)<br>Main filter unit (Down-stream): 1 disk of membrane having mean pore diameter of 5 µm (MEA/DMAEMA/HEMA = 90/5/5 treated) | $1.7*10^4$ | 90.2 | 95.4 |
| Example 2 | Pre-filter unit: 1 disk of membrane having mean pore diameter of 6 µm (untreated)<br>Main filter unit (Up-stream): 2 disks of membranes having mean pore diameter of 4 µm (untreated)<br>Main filter unit (Down-stream): 1 disk of membrane having mean pore diameter of 5 µm (DMAA/DMAEMA/HEMA = 92/3/5 treated) | $2.0*10^4$ | 91.1 | 95.8 |
| Comparative Example 9 | Pre-filter unit: 1 disk of membrane having mean pore diameter of 6 µm (untreated)<br>Main filter unit (Up-stream): 2 disks of membranes having mean pore diameter of 4 µm (untreated)<br>Main filter unit (Down-stream): 1 disk of membrane having mean pore diameter of 5 µm (untreated) | $2.6*10^6$ | 90.6 | 95.2 |
| Comparative Example 10 | Pre-filter unit: 1 disk of membrane having mean pore diameter of 6 µm (untreated)<br>Main filter unit (Up-stream): 2 disks of membranes having mean pore diameter of 4 µm (untreated)<br>Main filter unit (Down-stream): 4 disks of membranes having mean pore diameter of 4 µm (untreated) | $4.2*10^4$ | 78.7 | 91.8 |

As is obvious from Table 4, when increasing a number of disks (Comparative Example 10) to improve leukocyte untreated PP sheet and an untreated PET sheet to which the surface treating agent was not fixed were prepared.

The prepared sheets fixed with each surface treating agents and untreated sheets were subjected to platelet adhesion tests as follows. First, 50 mL of whole blood was collected into a blood collecting tube in which 7 mL of CPD liquid had been put. The blood in the tube was centrifuged at 1,200 rpm for 5 minutes to separate PRP (platelet rich plasma). After fractionating a portion of PRP, the remainder was further centrifuged at 3,000 rpm for another 10 minutes to obtain PPP (platelet poor plasma). Then, the first-fractionated PRP was diluted with PPP to adjust the number of platelet to $1*10^5$ cell/μL. 0.2 mL of diluted PRP was added gently dropwise on each sample. After leaving them to stand at room temperature for 30 minutes, the samples were rinsed twice with PSS (physiological saline solution). Then, the samples were immersed in 1 mass % PSS solution of glutaraldehyde and kept at room temperature for 1 hour. After the rinsing and drying, the samples were ion sputtered, and then observed on SEM (JEOL JSM-840) with taking photographs (1,000 times magnified, 5 views).

With changing blood samples, this procedure using fresh blood sample was repeated 3 times in total the platelet adhesion tests were subjected. The obtained mean platelet adhesion numbers are shown in Table 5 (PU sheet), Table 6 (PP sheet) and Table 7 (PET sheet) respectively. With respect to the morphology of platelet: the platelet that retained round shape was named "Type I", the platelet that had some pseudopods was named "Type II" and the platelet that extended lost the original shape was named "Type III".

TABLE 5

(PU sheet)

| surface treating agent | Composition of surface treating agent (mol %) | platelet adhesion numbers (cell/8.5*10$^{-3}$ mm$^2$) | | | |
|---|---|---|---|---|---|
| | | Type I | Type II | Type III | Total |
| Example 1 | MEA/DMAEMA/HEMA = 90/5/5 | 4.1 | 1.0 | 0.1 | 5.2 |
| Example 2 | DMAA/DMAEMA/HEMA = 92/3/5 | 2.7 | 0.8 | 0.4 | 3.9 |
| Example 3 | MEA/DEAEMA/HEMA = 98/1/1 | 1.3 | 1.1 | 0.6 | 3.0 |
| Example 4 | DMAA/DMAPMAm/HEMA = 70/15/15 | 4.2 | 3.1 | 1.8 | 9.1 |
| Example 5 | EEMA/DMAEMA/HEMA = 76/12/12 | 3.7 | 2.4 | 1.2 | 7.3 |
| Example 6 | MEA/DiPAEMA/HEMA = 87/10/3 | 2.9 | 1.7 | 0.4 | 5.0 |
| Example 7 | MEA/DMAEA/AEAAm = 90/5/5 | 2.2 | 1.3 | 0.7 | 4.2 |
| Example 8 | DMAA/DMAEMA/GMA = 90/5/5 | 3.9 | 1.6 | 0.8 | 6.3 |
| Comparative Example 1 | MEA/DMAEMA = 95/5 | 10.3 | 19.6 | 31.5 | 61.4 |
| Comparative Example 2 | DMAA/DMAEMA = 95/5 | 13.8 | 20.1 | 34.4 | 68.3 |
| Comparative Example 3 | MEA/HEMA = 95/5 | 16.5 | 10.9 | 0.4 | 27.8 |
| Comparative Example 4 | DMAA/DMAEMA/HEMA = 67/28/5 | 15.4 | 108.1 | 211.8 | 335.3 |
| Comparative Example 5 | DEAEMA/HEMA = 5/95 | 20.9 | 19.6 | 79.1 | 119.6 |
| Comparative Example 11 | Untreated PU porous membrane | 12.6 | 18.7 | 33.7 | 65.0 |

TABLE 6

(PP sheet)

| surface treating agent | Composition of surface treating agent (mol %) | platelet adhesion numbers (cell/8.5*10$^{-3}$ mm$^2$) | | | |
|---|---|---|---|---|---|
| | | Type I | Type II | Type III | Total |
| Example 1 | MEA/DMAEMA/HEMA = 90/5/5 | 5.8 | 1.9 | 0.5 | 8.2 |
| Example 2 | DMAA/DMAEMA/HEMA = 92/3/5 | 4.9 | 1.8 | 0.7 | 7.4 |
| Example 3 | MEA/DEAEMA/HEMA = 98/1/1 | 3.9 | 1.4 | 0.4 | 5.7 |
| Example 4 | DMAA/DMAPMAm/HEMA = 70/15/15 | 6.6 | 2.7 | 0.9 | 10.2 |
| Example 5 | EEMA/DMAEMA/HEMA = 76/12/12 | 6.1 | 2.1 | 1.3 | 9.5 |
| Example 6 | MEA/DiPAEMA/HEMA = 87/10/3 | 6.8 | 1.6 | 1.1 | 9.5 |
| Example 7 | MEA/DMAEA/AEAAm = 90/5/5 | 4.4 | 0.9 | 0.6 | 5.9 |
| Example 8 | DMAA/DMAEMA/GMA = 90/5/5 | 5.3 | 1.3 | 1.6 | 8.2 |
| Comparative Example 1 | MEA/DMAEMA = 95/5 | 6.3 | 11.9 | 673.7 | 691.9 |
| Comparative Example 2 | DMAA/DMAEMA = 95/5 | 2.1 | 0.2 | 721.5 | 723.8 |
| Comparative Example 3 | MEA/HEMA = 95/5 | 21.1 | 17.1 | 0.8 | 39.0 |
| Comparative Example 4 | DMAA/DMAEMA/HEMA = 67/28/5 | 4.0 | 89.9 | 281.9 | 375.8 |
| Comparative Example 5 | DEAEMA/HEMA = 5/95 | 10.9 | 28.9 | 88.1 | 127.9 |
| Comparative Example 12 | Untreated PP porous membrane | 0.7 | 1.2 | 711.3 | 713.2 |

TABLE 7

(PET sheet)

| surface treating agent | Composition of surface treating agent (mol %) | platelet adhesion numbers (cell/8.5*10$^{-3}$ mm$^2$) | | | |
|---|---|---|---|---|---|
| | | Type I | Type II | Type III | Total |
| Example 1 | MEA/DMAEMA/HEMA = 90/5/5 | 6.5 | 2.1 | 0.1 | 8.7 |
| Example 2 | DMAA/DMAEMA/HEMA = 92/3/5 | 6.2 | 0.8 | 0.3 | 7.3 |
| Example 3 | MEA/DEAEMA/HEMA = 98/1/1 | 6.2 | 1.8 | 0.1 | 8.1 |
| Example 4 | DMAA/DMAPMAm/HEMA = 70/15/15 | 5.9 | 2.6 | 1.2 | 9.7 |
| Example 5 | EEMA/DMAEMA/HEMA = 76/12/12 | 6.9 | 2.3 | 0.9 | 10.1 |
| Example 6 | MEA/DiPAEMA/HEMA = 87/10/3 | 7.2 | 3.4 | 1.6 | 12.2 |
| Example 7 | MEA/DMAEA/AEAAm = 90/5/5 | 7.8 | 2.1 | 0.2 | 10.1 |
| Example 8 | DMAA/DMAEMA/GMA = 90/5/5 | 6.2 | 1.2 | 0.5 | 7.9 |
| Comparative Example 1 | MEA/DMAEMA = 95/5 | 1.2 | 4.9 | 592.2 | 598.3 |
| Comparative Example 2 | DMAA/DMAEMA = 95/5 | 0.2 | 1.9 | 639.1 | 641.2 |
| Comparative Example 3 | MEA/HEMA = 95/5 | 18.9 | 10.8 | 0.2 | 29.9 |
| Comparative Example 4 | DMAA/DMAEMA/HEMA = 67/28/5 | 16.1 | 124.2 | 189.3 | 329.6 |
| Comparative Example 5 | DEAEMA/HEMA = 5/95 | 19.0 | 26.3 | 65.0 | 110.3 |
| Comparative Example 13 | Untreated PET porous membrane | 0.2 | 2.7 | 648.3 | 651.2 |

As is obvious from Tables 5 to 7, the PU, PP and PET sheets treated with the surface treating agents obtained in Examples 1 to 8 inhibited platelet adhesion better than the sheets treated with the surface treating agents of Comparative Examples 1 to 5 and the untreated sheets of Comparative Examples 11 to 13. Further, most of the adhered platelets retained round shape in the sheets of the present invention.

Test Example 7

Fixation to Stainless Plate

Stainless plates of 0.5 mm thickness and of 25 mm×50 mm were immersed in 0.1 mass % toluene (produced by Wako Pure Chemical Industries, Ltd.) solution of 3-glycidoxypropyltrimethoxysilane (KBM-403: produced by Shin-Etsu Chemical Co., Ltd.) overnight. Then the obtained plates were washed by toluene to rinse excessive 3-glycidoxypropyltrimethoxysilane. The washed plates were heated in an oven at 80° C. for 4 hours. Thus, stainless plates treated with the silane coupling agent were obtained.

In the same manner as in Test Example 1, the plates were fixed with the surface treating agents of Examples 1 to 5 respectively except that stainless plates treated with the silane coupling agent were used instead of the GMA-grafted PU porous membranes. The stainless plates fixed with the surface treating agents were washed by Soxhlet extraction-washing with methanol for 8 hours. The washed plates were observed on an X-ray optoelectronic spectrophotometer (JPS-905X, produced by JEOL Ltd.) to examine if iron atoms are present on the surface of the plates. As a result, no peak attributable to iron atom was observed in the plates. That is, it is confirmed that each of the plates are coated completely and fixed with the surface treating agent of each of the Examples.

DESCRIPTION OF REFERENCE NUMERALS

1 Blood treatment filter
2 Housing
3 Cover
4 Blood inlet port
5 Bottom
6 Blood outlet port
7 Filter unit
8 Blood inlet chamber
9 Blood outlet chamber

What is claimed is:

1. A surface treating agent fixed to a base material, wherein the surface treating agent comprises a copolymer of monomer components including:
a monomer (A) having a hydrophilic functional group of formula (1) below,
a monomer (B) having a basic functional group of formula (3) below, and
a monomer (C) having a reactive functional group of formula (7) below,
wherein the copolymer has a molar ratio of the monomer (A)/the monomer (B)/the monomer (C) being between 87/10/3 and 98/1/1,

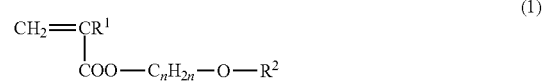

(1)

wherein R$^1$ represents a hydrogen atom or a methyl group, R$^2$ represents an alkyl group having 1 to 4 carbon atoms, n represents an integer of 2 to 4,

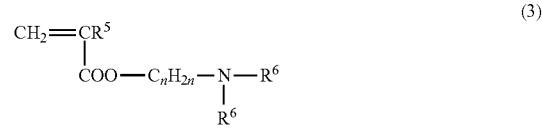

(3)

wherein R$^5$ represents a hydrogen atom or a methyl group, each of R$^6$s independently represents a hydrogen atom or an alkyl group having 1 to 4 carbon atoms, n represents an integer of 2 to 4,

(7)

wherein $R^7$ represents a hydrogen atom or a methyl group, n represents an integer of 0 to 3, and Y represents a hydroxyl group, an epoxy group, a primary amino group, a secondary amino group or a hydrogen atom.

2. The surface treating agent fixed to a base material according to claim 1, wherein the monomer (A) of formula (1) is 2-methoxyethyl(meth)acrylate or 2-ethoxyethyl(meth)acrylate.

3. The surface treating agent fixed to a base material according to claim 1, wherein the monomer (B) of formula (3) is N,N-dimethylaminoethyl(meth)acrylate, N,N-diethylaminoethyl(meth)acrylate, or N,N-diisopropylaminoethyl(meth)acrylate.

4. The surface treating agent fixed to a base material according to claim 1, wherein the monomer (C) of formula (7) is 2-hydroxyethyl(meth)acrylate or glycidyl(meth) acrylate.

5. A filtering material for filter, wherein at least a part of a base material of the filtering material is coated with the surface treating agent according to claim 1.

6. A blood treatment filter comprising:
a housing having a blood inlet port and a blood outlet port, and
a filter unit which partitions interior of the housing into a blood inlet chamber and a blood outlet chamber,
wherein at least a part of the filter unit is made of the filtering material for filter according to claim 5.

* * * * *